United States Patent [19]

Gadó et al.

[11] 4,363,876
[45] Dec. 14, 1982

[54] MICROMONOSPORA CULTURE

[75] Inventors: István Gadó; Antónia Jekkel née Bokány; Gyuml/o/ rgy Szvoboda; Miklós Járai; Sándor Piukovich, all of Budapest; Sándor Istvan, Szentendre, all of Hungary

[73] Assignee: Chinoin Gyogyszer es Vegyeszeti Termekek Gyara R.T., Budapest, Hungary

[21] Appl. No.: 116,915

[22] Filed: Jan. 30, 1980

[30] Foreign Application Priority Data

Feb. 6, 1979 [HU] Hungary .............................. CI 1911

[51] Int. Cl.³ ........................... C12N 1/20; C12R 1/29

[52] U.S. Cl. ...................................... 435/253; 435/867
[58] Field of Search ........................ 435/80, 253, 867

[56] References Cited

U.S. PATENT DOCUMENTS 3,832,286  8/1974  Weinstein et al. .................... 435/80
3,956,068  5/1976  Weinstein et al. .................... 435/80

Primary Examiner—Alvin E. Tanenholtz
Attorney, Agent, or Firm—Hubbell, Cohen, Stiefel & Gross

[57] ABSTRACT

A culture of *Micromonospora rosea* capable of producing the antibiotic sisomicin.

2 Claims, No Drawings

MICROMONOSPORA CULTURE

This application relates to a novel microbiological method for producing a heretofore known antibiotic, sisomicin and its pharmaceutically acceptable salts by cultivating a new species of Micromonospora, i.e. *Micromonospora rosea*.

Sisomicin (or Antibiotic 66-40)(0-2,6-diamino-2,3,4,6-tetradeoxy-α-D-glyero-hex-4-enopyranosyl/1→4/-O-(3-deoxy-4-C-methyl-3-(methylamino)-β-L-arobinopyranosyl/1→6//-2-deoxy-D-streptamin).

Sisomicin is a broad spectrum antibiotic, which has an adverse effect upon the growth of Gram-positive and Gram-negative bacteria.

There are several microbiological methods known for its production. It is produced for example as main product by cultivating *Micromonospora inyoensis* NRRL 3292 (U.S. Pat. Nos. 3,932,286 and 3,907,771) or together with verdamicin by cultivating *Micromonospora grisea* NRRL 3800 (U.S. Pat. No. 3,951,746) or together with Antibiotic G-52 by the cultivation of *Micromonospora zionensis* NRRL 5466 (U.S. Pat. No. 3,956,068) or together with gentimicin by cultivating *Micromonospora purpurea* var. nigrescens MNG 00122 (Hungarian Pat. No. 168,778).

The novel microorganism used according to this invention for the production of sisomicin was isolated from a Hungarian soil sample. This strain, which is different from any other microorganism and has the ability to produce sisomicin has been classified as a new species of Micromonospora and it has been named *Micromonospora rosea* species nova. From this microorganism the strain S1/109 was obtained with various Greeding procedures. A culture of the living organism, *Micromonospora rosea* S1/109 has been deposited on Dec. 12, 1978 at the National Collection of Microorganisms in Budapest, where it has been assigned accession number MNG 00 182. By its cultivation a fermentation medium of high sisomicin content is achieved.

As mentioned earlier the invention relates to a novel process which comprises cultivating *Micromonospora rosea*, advantageously the strain MNG 00182 in an aqueous nutrient medium containing assimilable sources of nitrogen and carbon and inorganic salts under submerged aerobic conditions and if desired isolating the sisomicin therefrom and separating it from the accompanying antibiotics, purifying it and/or if desired turning it into one of its pharmaceutically acceptable salts.

The deposited microorganism, *Micromonospora rosea* S1/109 has the microscopic, macroscopic and biochemical properties set forth below.

MORPHOLOGY a. Macroscopic observations of 10 day old culture incubated at 37° C. Czapek's Agar show fair growth with no aerial mycelium, no diffusible pigment, well developed, regular, round colonies, orange-blick colour.

b. Microscopic observations of the organism show 1 ng, branched, regular filaments without dividing wall, which are $0.5\mu$ in diameter. Spores are produced on simple sporophores of $1-1.5\mu$ in diameter and are spherical to ovoid in shape.

BIOCHEMICAL AND PHYSIOLOGICAL PROPERTIES

The strain *Micromonospora rosea* S1/109 shows good growth at 28°–37° C. and no growth occurs at 44° C.

The utilization of carbon source was tested in a nutrient medium consisting of 0.5% yeast extract, 1% carbon source, 0.1% calcium carbonate, 1.5% agar all in distilled water.

In Table I there are set forth observations on carbon utilization:

TABLE I

| | Carbon Utilization |
|---|---|
| Carbon source | *Micromonospora rosea* S1/109 |
| Arabinose | poor |
| Ribose | fair |
| Rhamnose | poor |
| Xylose | good |
| Fructose | good |
| Galactose | moderate |
| Glucose | good |
| Lactose | poor |
| Sucrose | good |
| Raffinose | moderate-poor |
| Dulcitol | moderate-poor |
| Mannitol | poor |
| Inositol | poor |
| Starch | good |

The nitrogen utilization was tested in a nutrient medium consisting of 1% glucose, 1.5% agar and a nitrogen source as indicated in Table II, all in distilled water. In Table II nitrogen utilization is set forth.

TABLE II

| | Nitrogen Utilization |
|---|---|
| Nitrogen source | *Micromonospora rosea* S1/109 |
| 0,5% Yeast extract | good |
| 1% Asparagine | moderate-poor |
| 1% Glutamic acid | poor |
| 1% Ammonium nitrate | poor |
| 1% NZ Amine | good |

A growing colony of *Micromonospora rosea* will hydrolyse gelatin, milk and starch and reduce nitrate to nitrite. The microorganism will tolerate a maximum of 2% sodium chloride in a growth medium.

CULTURAL CHARACTERISTICS

In Table III there are set forth culture characteristics of *Micromonospora rosea* S1/109 (In describing the color formations for this observations the following reference is employed: Baumanns Farbtonkarte Atlas II. Paul Baumann, Aue I-SA 87350 LAu 302, GFR).

TABLE III

| | Cultural Characteristics |
|---|---|
| Medium | *Micromonospora rosea* S1/109 |
| Glucose asparagine agar | no growth |
| Pepton iron agar | Growth poor; dirty yellow, turning into grey; Co 40. Little spore-layer: Co 63. No diffusible pigment |
| Emerson's agar | Growth poor; 1–2 colonies, color: orange, vivid, slightly brownish, 0 126, or Oc 117 |
| Glucose-yeast extract agar | Growth: fair; color: vivid orange, turning into black, strongly plicate colonies; Oc 98-Oc 120, and later 8 |
| Nutrient agar | Growth: fair; color: vivid orange, turning into black; |

TABLE III-continued

| Medium | Cultural Characteristics |
|---|---|
| | *Micromonospora rosea* S1/109 |
| Tyrosine agar | Oc 98-Oc 120, and later 8 Growth: very poor; color: grayish white, in some places black; 8, pink soluble pigment, Oc 101 |
| Czapek's agar | Growth: fair; color: vivid orange and later black; Oc 97-Oc 120, and later 8 |
| Bennet's agar | Growth: fair; color: pale orange, turning into brown; Oc 97-Oc 119 or 120, weak brown soluble pigment |
| Potato plug (without calcium carbonate) | Growth: in traces color: orange; Oc 96 |
| Potato plug (with calcium carbonate) | Growth: in traces or very poor; color: orange; Oc 96-97 and 99 |

By comparison of the above identifying characteristics of the strain S1/109 with Luedemann's Micromonospora system the strain can be classified as a new species of Micromonospora.

According to a preferred embodiment of the invention the microorganism *Micromonospora rosea* S1/109 is cultivated under submerged conditions.

The nutrient medium can obtain various assimilable sources of carbon and nitrogen, inorganic salts, trace elements and antifoam agents. Exemplary of assimilable carbon and nitrogen sources, respectively energy sources are soybean meal, soybean hydrolysate, casein hydrolysate, corn steep liquor, yeast extract and different carbohydrates, such as glucose, starch, soluble starch, dextrin and the like. Preferred inorganic salts are for example ferrous, magnesium and cobalt salts. To increase the buffer capacity of the nutrient medium preferably calcium carbonate is added. As antifoam agents plant oils can be used (for example palm oil, sunflower oil and soybean oil).

By combination of the various components of the nutrient medium different nutrient broths can be obtained. The medium used for shake flask or inoculum fermentation is different from that used for the main fermentation.

The microorganism is grown most advantageously in a nutrient medium consisting of soybean meal, pepton or casein hydrolysate, potato or corn starch, dextrin or soluble starch, glucose, calcium carbonate, ferrous and magnesium sulfate, cobalt nitrate and palm oil.

Production of sisomicin can be effected between 25°–40° C., preferably at 28°–33° C. Agitation is between 200–400 r.p.m. Air input is preferably 1/1 v/v pro minute.

In order to assay the total antibiotic activity (sisomicin and minor antibiotics) during the fermentation Staphylococcus epidermidis is employed as test organism. The assay is run against a standard preparation of sisomicin using agar diffusion method.

The total activity of the fermentation medium in 100–130 hours is about 600–700 U/ml (1U=1 μg/ml activity of sisomicin base).

85% of the antibiotics in the fermentation medium is sisomicin.

When peak antibiotic activity is attained, the sisomicin is isolated by combination of steps known in the art. The obtained sisomicin base, if desired, is turned into its pharmaceutically acceptable salts.

The quantity of the sisomicin produced under laboratory circumstances is over 700–800 μg/ml and in pilot scale, i.e. 1 m³ fermentation tank it is 600–700 μg/ml.

The antibiotic concentration is more than three times that described in U.S. Pat. No. 3,832,286 which is considered hitherto the best result. The fermentation medium contains only 15% or less accompanying antibiotics beside sisomicin.

The following examples illustrate the best mode for carrying out this invention.

EXAMPLES

1. Add 1 ml of the vegetative mycelia (stored deep-frozen at −20° C.) of the strain *Micromonospora rosea* S1/109 (MNG 00182) under asseptic conditions to a 3000 ml Erlenmeyer flask containing 800 ml of the following sterile medium:

| | |
|---|---|
| Tryptone (oxoide) | 5 g |
| Soybean meal | 10 g |
| Soluble starch | 20 g |
| Glucose | 1 g |
| Calcium carbonate | 2 g |
| Tap water to | 1000 ml |

Prior to sterilizing the medium, adjust its pH to 7.0. Incubate the fermentation medium for 3 days at 28° C. on a rotary shaker (260 r.p.m., 10 cm stroke). Inoculate with the medium obtained 100 liters of the following sterile medium under aseptic conditions:

| | |
|---|---|
| Soybean meal | 10 g |
| Casein hydrolysate (dry weight) | 5 g |
| Potato starch | 22 g |
| Glucose | 10 g |
| Calcium carbonate | 2 g |
| Palm oil | 2 g |
| Tap water to | 1000 ml |

Casein is hydrolysed with pancreatine. Adjust the pH of the medium, prior to sterilizing, to 7.0. Aerobically ferment for 36–48 hours at 30° C., while stirring at 400 r.p.m. with air input 1/1 v/v. Palm oil is used as antifoam agent. Use 10 liters of the medium obtained for the inoculation of 100 liter fermentation medium of the following composition:

| | |
|---|---|
| Soybean meal | 40 g |
| Pepton | 10 g |
| Potato starch | 10 g |
| Dextrin | 25 g |
| Glucose | 5 g |
| Calcium carbonate | 4 g |
| Magnesium sulfate (7H$_2$O) | 2 g |
| Ferrous sulfate (7H$_2$O) | 0,2 g |
| Cobalt nitrate (6H$_2$O) | 0,8 mg |
| Palm oil | 2 g |
| Tap water to | 1000 ml |

Prior to sterilizing the aforedescribed medium, adjust the pH to 8.0. Sterilize for 1 hour at 121° C., under 1.3–1.4 at pressure with stirring. Use a fermentation tank of stainless steel. Stir at 400 r.p.m. with air input at 1/1 v/v. Use palm oil as antifoam agent.

Antibiotic production starts after 35–40 hours and reaches its maximum after 110–120 hours of fermentation. The time for finishing the fermentation is determined by a fast turbidimetric procedure applying *Kleb-* siella pneumoniae (F. Kavanagh: Dilution Methods of Antibiotic Assay, Analytical Microbiology, Acad. Press, New York, pp. 125-140, /1963/).

The quantity of the antibiotic produced reaches at the end of the fermentation 650 U/ml (1U is equivalent to the standard efficiency of 1 μg sisomicin base as determined with Staphylococcus epidermidis test organism by the agar diffusion method (J. S. Simpson: Analytical Microbiology, Acad. Press, New York, pp. 87-124,/1963/).

2. Under aseptic cnditions, add 1 ml of the vegetative mycelia (stored deep-frozen at −20° C.) of the strain *Micromonospora rosea* S1/109 (MNG 00 182) to a 3000 ml Erlenmeyer flask containing 800 ml of the following sterile medium:

| | |
|---|---|
| Tryptone (oxoide) | 5 g |
| Soybean meal | 10 g |
| Soluble starch | 20 g |
| Glucose | 1 g |
| Calcium carbonate | 2 g |
| Tap water to | 1000 ml |

Prior to sterilizing the medium, adjust its pH to 7.0. Incubate the fermentation medium for 3 days at 28° C. on a rotary shaker (260 r.p.m., 10 cm stroke). Inoculate with the medium obtained 100 liters of the following sterile medium under aseptic conditions:

| | |
|---|---|
| Soybean meal | 10 g |
| Sucrose | 10 g |
| Potato starch | 10 g |
| Calcium carbonate | 4 g |
| Palm oil | 2 g |
| Tap water to | 1000 ml |

Adjust the pH of the medium prior to sterilizing to 7.0. Aerobically ferment for 48-60 hours at 30° C., while stirring at 400 r.p.m. with air input at 1/1 v/v. Use palm oil as antifoam agent. Inoculate with the medium obtained 1 m³ of the fermentation culture medium of the following composition:

| | |
|---|---|
| Soybean meal | 40 g |
| Pepton | 10 g |
| Potato starch | 10 g |
| Dextrin | 25 g |
| Glucose | 5 g |
| Calcium carbonate | 4 g |
| Magnesium sulfate (7H$_2$O) | 2 g |
| Ferrous sulfate (7H$_2$O) | 0,2 g |
| Cobalt nitrate (6H$_2$O) | 0,8 mg |
| Palm oil | 2 g |
| Tap water to | 1000 ml |

Prior to sterilizing the aforedescribed medium, adjust the pH to 8.0. Sterilize for 1 hour at 121° C., under 1.3-1.4 at pressure, with stirring. Use a fermentation tank of stainless steel. Stir at 400 r.p.m. with air input at 1/1 v/v. Use palm oil as antifoam agent.

Antibiotic production starts after 35-40 hours and reaches its maximum after 110-120 hours of fermentation. The time for finishing the fermentation is determined by the fast turbidimetric procedure applying *Klebsiella pneumainae*.

The quantity of the antibiotic produced reaches at the end of the fermentation 600 U/ml (agar diffusion method was used).

3. Transfer 100 liters of the inoculum according to Example 1 to 1 m³ fermentation medium of the following composition:

| | |
|---|---|
| Soybean meal | 40 g |
| Casein hydrolysate (dry weight) | 10 g |
| Potato starch | 10 g |
| Dextrin | 25 g |
| Glucose | 5 g |
| Calcium carbonate | 4 g |
| Magnesium sulfate (7H$_2$O) | 2 g |
| Ferrous sulfate (7H$_2$O) | 0,2 g |
| Cobalt nitrate (6H$_2$O) | 0,8 mg |
| Palm oil | 2 g |
| Tap water to | 1000 ml |

Hydrolyse casein with pancreatine. Adjust the pH of the medium, prior to sterilizing, to 8.0. Sterilize for 1 hour at 121° C., under 1.3-1.4 at pressure with stirring. Use a fermentation tank of stainless steel. Stir at 400 r.p.m. with air input at 1/1 v/v. Use palm oil as antifoam agent.

Antibiotic production starts after 35-40 hours and reaches its maximum after 110-120 hours of fermentation. The time for finishing the fermentation is determined by a fast turbidimetric procedure applying *Klebsiella pneumoniae*.

The quantity of the antibiotic produced reaches at the end of the fermentation 650 U/ml (agar diffusion method was used).

4. Transfer 100 liters of the inoculum medium according to Example 1 to 1 m³ fermentation medium of the following composition:

| | |
|---|---|
| Soybean meal | 40 g |
| Casein hydrolysate (dry weight) | 10 g |
| Corn starch | 50 g |
| Glucose | 5 g |
| Calcium carbonate | 4 g |
| Magnesium sulfate (7H$_2$O) | 2 g |
| Ferrous sulfate (7H$_2$O) | 0,2 g |
| Cobalt nitrate (6H$_2$O) | 0,8 mg |
| Palm oil | 2 g |
| Tap water to | 1000 ml |

Hydrolyse casein with pancreatine. Adjust the pH of the medium, prior to sterilizing, to 8.0. Sterilize for 1 hour at 121° C, under 1.3-1.4 at pressure with stirring. Use a fermentation tank of stainless steel. Stir at 400 r.p.m. with air input at 1/1 v/v. Use palm oil as antifoam agent.

Antibiotic production starts after 35-40 hours and reaches its maximum after 110-120 hours of fermentation. The time for finishing the fermentation is determined by a fast turbidimetric method applying *Klebsiella pneumoniae*.

The quantity of the antibiotic produced reaches at the end of the fermentation 680 U/ml (agar diffusion method was used).

At the end of the fermentation pure sisomicin is isolated by steps known in the art.

M.P.: 198°–201° C.; $(\alpha)_D = +188°$ (c=0.3 water)

IR spectrum (KBr): $\nu$OH, NH 3170-3360, $\nu$CH=COC 1690, $\nu$COC 1060 cm$^{-1}$ PMR spectrum (D$_2$O): $\delta$1.20 (Me-4″, s, 3H), $\delta$2.50 (Me-N-3″, s, 3H), $\delta$2.56 (H-3″, d, $J_{2″,3″}$=10 Hz, 1H), δ3.17 (H-6', bs, 2H), δ3.30 (H$_{ax}$−5", d, J$_{gem}$=12 Hz, 1H), δ3.80 (H-2", dd, J$_{2",3"}$=10 Hz, J$_{1",2"}$=4 Hz, 1H), δ4.04 (H$_e$-5", d, J$_{gem}$=12 Hz, 1H), δ4.88 (H-4', bt, 1H), δ5.09 (H-1", d, J$_{1",2"}$=4 Hz, 1H), δ5.35 (H-1', d, J$_{1',2'}$=2 Hz, 1H) ppm.

Mass spectrum: molecular weight: 447

Mass number of the characteristic ions: (m/e): 447, 332, 304, 160, 145, 127, 118, 110, 100.

5. Production of sisomicin sulfate

Dissolve 15 g of pure sisomicin base in 60 ml of deionised water and adjust the pH to 4.3 with 5 N sulfuric acid. Stir the solution with 1.5 g of activated charcoal for 30 minutes and filter with Seitz sheet. Wash the filter three times with 5 ml of deionised water and add the combined filtrates to 1 liter of methanol under vigorous stirring. Store the solution in a cool room and filter the resulting precipitate. Wash the obtained sisomicin sulfate three times with 50 ml of methanol and dry it in vacuum at 50° C. over phosphorous pentoxide obtaining 22 g of sisomicin sulfate.

We claim:

1. A substantially biologically pure culture of the *Micromonospora rosea* species having the capability of producing sisomicin upon cultivation in an aqueous nutrient medium.

2. A substantially biologically pure culture of the strain *Micromonospora rosea* MNG 00182 having the capability of producing sisomicin upon cultivation in an aqueous nutrient medium.

* * * * *

UNITED STATES PATENT AND TRADEMARK OFFICE
CERTIFICATE OF CORRECTION

PATENT NO. : 4,363,876
DATED : Dec. 14, 1982
INVENTOR(S) : István Gadó et al.

It is certified that error appears in the above—identified patent and that said Letters Patent is hereby corrected as shown below:

Column 1, lines 63-64: "lng" should read --long--.

Column 7, line 2: "$J_{2"3"}$" should read --$J_{2",3"}$--.

Signed and Sealed this

Seventeenth Day of April 1984

[SEAL]

Attest:

GERALD J. MOSSINGHOFF

Attesting Officer     Commissioner of Patents and Trademarks